United States Patent [19]
Rainey

[11] Patent Number: 6,093,021
[45] Date of Patent: Jul. 25, 2000

[54] PARALLEL AIR STREAM DENTAL AIR-ABRASION SYSTEM

[76] Inventor: J. Tim Rainey, P.O. Box 1044, Refugio, Tex. 78377

[21] Appl. No.: 08/882,653

[22] Filed: Jun. 25, 1997

[51] Int. Cl.7 .................................................... A61C 3/02
[52] U.S. Cl. .............................................................. 433/88
[58] Field of Search ............................... 433/88, 89, 216; 51/439, 410, 436, 321

[56] References Cited

U.S. PATENT DOCUMENTS

| | | |
|---|---|---|
| Re. 30,536 | 3/1981 | Perdreaux, Jr. . |
| 1,213,144 | 1/1917 | Baekeland . |
| 1,216,272 | 2/1917 | Berry . |
| 2,147,394 | 2/1939 | Austern . |
| 2,766,558 | 10/1956 | Black . |
| 3,075,288 | 1/1963 | Balamuth et al. . |
| 3,076,904 | 2/1963 | Kleesattel et al. . |
| 3,213,537 | 10/1965 | Balamuth et al. . |
| 3,654,540 | 4/1972 | Honig et al. . |
| 3,822,638 | 7/1974 | Merkin . |
| 3,956,826 | 5/1976 | Perdreaux, Jr. . |
| 3,972,123 | 8/1976 | Black . |
| 4,051,337 | 9/1977 | Warrin . |
| 4,174,571 | 11/1979 | Gallant . |
| 4,412,402 | 11/1983 | Gallant . |
| 4,487,582 | 12/1984 | Warrin . |
| 4,494,932 | 1/1985 | Rzewinski . |
| 4,522,597 | 6/1985 | Gallant . |
| 4,635,897 | 1/1987 | Gallant . |
| 4,708,534 | 11/1987 | Gallant . |
| 4,733,503 | 3/1988 | Gallant et al. . |
| 4,820,152 | 4/1989 | Warrin et al. . |
| 4,893,440 | 1/1990 | Gallant et al. . |
| 5,275,561 | 1/1994 | Goldsmith . |
| 5,330,354 | 7/1994 | Gallant . |
| 5,350,299 | 9/1994 | Gallant . |
| 5,525,058 | 6/1996 | Gallant et al. . |
| 5,746,596 | 5/1998 | Gallant et al. . |

OTHER PUBLICATIONS

Airbrasive: some fundamentals by Robert B. Black, D.D.S., Reprinted from The Journal of the American Dental Association, vol. 41, pp. 701–710, Dec. 1950.

No drill, no needles by Brian B. Crecente, Albany Democrat–Herald, People Section, Mar. 8, 1995, p. B7.

Kreative, Inc. Presents KV–1 to the Dental Profession.

HP Series, The Perfect Solution . . . by Texas Airsonics, Inc.

The first micro air–abrasion unit, Business Watch Magazine, p. 8, Oct. 1994.

*Primary Examiner*—Nicholas D. Lucchesi
*Attorney, Agent, or Firm*—Royston, Rayzor, Vickery, Novak & Druce, L.L.P.

[57] ABSTRACT

A dental air-abrasion system having at least one air source for supplying pressured air to at least a primary air passageway and a secondary air passageway. The primary air passageway has an inlet conduit that establishes fluid communication between the air source and a venturi cup. The venturi cup is capable and intended to contain abrading particulate to be suspended in a primary air flow passing within the primary air passageway. The primary air passageway also has an exit conduit establishing fluid communication between the venturi cup and a manifold. The secondary air passageway includes a bypass conduit establishing fluid communication between the air source and the manifold. The manifold provides a fluid juncture for joining the primary air passageway with the secondary air passageway into a single uniform particulate delivery passageway. The uniform particulate delivery passageway terminates in a dispensing tip. Optionally, the air source includes a purifier for cleansing supplied air before its introduction into the air passageways. An agitator may also be coupled to the venturi cup for preventing compaction of abrading particulate in the venturi cup to assure suspension of the abrading particulate in the air flow passing from the venturi cup into an exit conduit. Further, an abrading particulate sensing means is directed across at least one conduit downstream from the venturi cup for sensing the amount of abrading particulate picked up from the cup.

22 Claims, 1 Drawing Sheet

PARALLEL AIR STREAM DENTAL AIR-ABRASION SYSTEM

FIELD OF THE INVENTION

The present invention relates generally to dentistry. More particularly, it relates to dental devices used to abrade teeth.

BACKGROUND OF THE INVENTION

The art of dentistry has been practiced for centuries. Initially, primitive instruments were used to manipulate a person's teeth for purposes of extraction and the like. Unfortunately, most of the procedures and operations performed by dentists were painful and there were few means for minimizing this pain. As the science of dentistry progressed, more was learned about oral care and associated implements and tools were developed to facilitate the operating dentist. One problem, however, still lingers for dentist and patient, and that is that a substantial degree of pain and discomfort remains associated with dental visits. Though significant strides have been made in these regards, and whether or not the discomfort associated with dental procedures is real or assumed by the patient, there is still a great deal of apprehension experienced by a person in anticipation of a visit to the dentist.

Together with other types of surgical procedures, the science of dentistry has been successful in alleviating extreme pain associated with dental procedures. Discomfort, however, is still a common experience of dental patients and an obstacle to dental care that dentists wish to diminish. A substantial hurdle that dentists have had to overcome is the fact that teeth are complex structures comprised of very hard outer surfaces that protect softer and extremely sensitive interiors. As a result, great force has been traditionally employed and applied to mechanical abrading instruments to penetrate and prepare the hard outer coating of the teeth. Consequently, extreme care must be used by the dentist to only abrade the outer surface without conflicting with the sensitive core of the tooth.

Most dental procedures are performed while the patient is conscious, but local anesthetics are administered to the effected area to mask the potentially extreme pain that could otherwise be experienced. Necessarily, several uncomfortable "evils" still plague people's perceptions of dental visits. The first is the expectation of at a minimum, receiving an uncomfortable shot in the mouth that produces a strange numb feeling that lingers after the procedure, slowly wearing off in due time after leaving the dentist's office. Secondly, several other disdainful experiences stem from the relatively high pressures applied upon the teeth. One such effect or result is frictionally produced heat associated with conventional mechanical drilling and abrading processes. In many instances, the dentist must apply heavy mechanical force in terms of rotary instrumentation in order to penetrate the hard outer surface. The penetration of enamel with rotary instrumentation is painful without anesthesia. Even with local anesthetic, the obnoxious vibration and sound associated with rotary drills is uncomfortable at best, and causes apprehension in the patient. Furthermore, the instruments that have been traditionally used in these procedures are high speed and slow speed rotary drills. A significant amount of friction is caused by the action of the instrument on the tooth resulting in heat and an associated burning or "hot" malodor. The heat must be dissipated prior to reaching uncomfortable levels and the smell is something the patient must endure. Patients also experience discomfort caused by vibration of the rotary instruments that manifest as bone-conducted noise that can be very irritating during treatment.

The drilling and abrading of a tooth normally serves a dual purpose. The first is to remove undesirable portions of the tooth such as hypocalcified enamel, decay or old filling material. The second is to prepare the revealed surface of the tooth for receiving a filler or coating material that will protect the affected area in the future. An often encountered problem is that the mechanical means for wearing portions of the tooth away are not exact and produce a variable surface corresponding to the shape of the rotary bur and which often creates sharp edges and recesses at their intersections. These effects of rotary instrumentation are undesirable for at least three reasons. The first is that the resulting apexes establish stress concentration points within the tooth structure thereby compromising its inherent solidarity. The second is that the vibration and heat from high speed rotary instrumentation creates crack and craze lines in the enamel and dentin of the tooth leading to more pathology. Thirdly, rotary instrumentation also creates a "smear" layer of indiscriminant ground particles on the surface which acts as a contaminant.

In response to the above outlined detrimental effects associated with conventional drilling and grinding dental instruments and techniques, alternatives have been developed. One such alternative is generally referred to as air-abrasion systems. These systems capitalize on characteristics that can best be understood as a highly focused "sandblasting" of the tooth. A forceful stream of particles can be directed upon a tooth to either affect its surface, or by more prolonged use to cut portions of the tooth away. This method can be utilized much like a mechanical drill or rotary abrading instrument. It is even possible for this tool to be used to erode interior portions of the tooth after access is provided through a penetrating porthole.

Implementation of such air-abrasion systems occurred in dentistry at least as early as the 1950's. These early systems, however, were cumbersome and often were inexact with respect to the particulate matter applied to the tooth. These are critical parameters because they determine the effectiveness of the treatment and the willingness of dentists to employ them. They also negatively affect accuracy of the procedures. There were also mechanical deficiencies within the design of the early systems that often prohibited the suspension of a proper and consistent amount of particulate in an air stream. Blockages could also form in the passages if plugs of particle mass were accidentally picked up in the system and transported through necked regions of the delivery system. Still further, the early systems were expensive and not well understood; therefore, conventional dentistry did not heartily embrace the concept and the process never enjoyed much success.

SUMMARY OF THE INVENTION

The application of the present invention is conceptually based on the early air-abrasion systems and similar benefits may be derived therefrom. In modern dentistry, there are specific occasions when the preparation of the tooth by air abrasion is particularly advantageous. One such instance is adhesive restorative dentistry. These and related procedures are more generally referred to by the public as "bonding". They are gaining acceptance and popularity and are therefore more often requested by patients and are favored by dentists. The methods by which these protective materials adhere to the tooth's surface vary and include chemical, mechanical and ionic bonding. One thing all have in common, however, is that each bonds best to a clean, mechanically etched and roughened surface. That is, one just like that left by an air-abrasion system.

The air-abrasion system of the present invention also exploits the same advantages discovered with respect to the early systems. Air-abrasion can be explained as essentially a non-mechanical method of treating teeth which employs the use of kinetics for its action. That is, it is the utilization of minute particles that because of their very small size can be projected at the tooth surface with extremely high velocities and momentums. But because of the infinitesimal size and commensurately small mass of the individual particles with respect to the tooth upon which it is directed, the patient experiences little or no sensation as a result of the air abrading process. Aside from this enhancement over conventional rotary drilling and abrading wherein little or no physical pressing force is felt by the patient, the air-abrasion systems produce little or no heat or the accompanying burning smell. Moreover, a continuous surface devoid of sharp angles may be easily established using an air-abrasion system.

While the present invention enjoys many of the resulting benefits of presently known air-abrasion systems, its design and structure embody new concepts for efficiently and consistently delivering a variably controllable stream of abrasive particles for direction upon a receiving tooth structure. This is accomplished by combining two flows of air from a single source; a first air flow that passes through a particle suspension source at a relatively slow velocity and low volume, and a second flow that bypasses the particle suspension source, but into which the particle carrying first flow is deposited. It is the resulting combined air stream that is jetted from the device and directed upon the tooth structures.

A primary drawback of previously known air-abrasion systems was their unreliability with respect to dispensed particle velocity and content. Because of the possible uncontrollable variability of the particle content of the exiting stream, the dentist could not rely on achieving consistent cutting characteristics upon a tooth structure. The present invention has been designed in response thereto.

There are several known means for suspending particles in an air stream including spiral feed mechanisms, venturi powder delivery systems and gravity feed mechanisms. The venturi cup type is the least expensive, but it is also the most unreliable with respect to consistency in rate of particulate suspended in a given air flow. This invention capitalizes on the inexpensive nature of the venturi cup and incorporates enhancements that control and establish delivery of an air steam that is uniformly laden with particulate. This is accomplished by dividing a single air source into two distinct and independently controllable air flows. By using a single air source, similar pressure will be carried in each of the two flows. The first or primary air flow is diverted to a venturi cup where abrading particles are contained and suspended into the primary air flow through a venturi orifice. Under conventional design, the entire air flow passed through the venturi cup and the orifice had to have a diameter of about one-half the diameter of the dispensing or cutting tip of the air-abrasion system. This was problematic in that the diameter of the venturi orifice would then only be about 0.007 inches, or one-half of a typical 0.015 inch diameter cutting tip. As such, the 25–50 micron (about 0.001–0.002 inches) abrading particles often plugged the venturi orifice halting the cutting process. Keeping particles suspended and in motion required an expensive vibrator mechanism.

In the present invention, the secondary air flow bypasses the venturi cup and rejoins the primary air flow at a juncture downstream of the cup. In this manner, as compared to a conventional design, less of the total air flow to be delivered at the cutting tip must pass through the venturi orifice. This dilution effect of the particle laden air stream permits the utilization of a larger venturi orifice size that is less likely to become plugged by the abrading particulate.

To assure that a consistent rate and mix of abrading particle laden air is being dispensed from the cutting tip, an automated monitoring and control system is utilized. The amount of particulate suspended in the primary air stream is measured downstream from the venturi cup by such means as an electronic sensor or ultrasonic turbidity meter. This "density" is analyzed and either or both of the air streams may be adjusted to affect a uniform dispensation of suspended particulate at the cutting tip. By these monitoring and control mechanisms the unpredictability of the conventionally configured venturi cup is alleviated. Previously, variabilities caused by changes in atmospheric pressure, humidity and a decreasing level of particulate in the retaining cup were difficult, if not impossible to control. Still further, it is contemplated that the venturi cup of the present invention may be optionally agitated using ultrasonics or an air reed agitator to assist in the take-up or suspension process of the particulate in the venturi cup. Further yet, it is contemplated that the source of the ultrasonic agitation may be commonly from that used to produce ultrasonic waves utilized in the turbidity or density detection unit downstream therefrom. In summary, the present invention provides an improved method for utilizing and controlling the inexpensive venturi cup technology in dental procedures resulting in accurate delivery rates of particulate in a suspension air stream measurable in grams per minute. Accordingly, the following exemplary, preferred and optional embodiments are disclosed.

In at least one embodiment, the present invention may be characterized as a dental air-abrasion system having at least one air source for supplying pressured air to at least a primary air passageway and a secondary air passageway. The primary air passageway has an inlet conduit that establishes fluid communication between the air source and a venturi cup. The venturi cup is capable and intended to contain abrading particulate to be suspended in a primary air flow passing within the primary air passageway. The primary air passageway also has an exit conduit establishing fluid communication between the venturi cup and a manifold. In the case of the dental air-abrasion system, the fluid is of course in the form of an air stream. The secondary air passageway includes a bypass conduit establishing fluid communication between the air source and the manifold. The manifold provides a fluid juncture for joining the primary air passageway with the secondary air passageway into a single uniform particulate delivery passageway that terminates in a dispensing tip. The design of the air-abrasion system is such that the flow of air through each of the primary and the secondary air passages is controllable. It is possible that a variable amount of air, including no flow, may be directed through either of the passageways.

The primary and the secondary air passageways together form a parallel air flow path between the air source and the manifold. At least one air source may be a single common air source that is in simultaneous fluid communication with both of the primary and secondary air passageways. The air source also may include a purifier for cleansing supplied air before the air is introduced into the primary and secondary air passageways.

The system may also include an ultrasonic agitator directed at the venturi cup for preventing compaction of abrading particulate in the venturi cup and for facilitating suspension of the abrading particulate in an air flow passing out of the venturi cup into the exit conduit. The venturi cup additionally may include a particulate inlet through which additional abrading particulate is addable to the venturi cup during operation of the dental air-abrasion system.

An abrading particulate sensing means directed across the exit conduit is provided for sensing the amount of abrading particulate present in a detection zone within the exit conduit. In one optional embodiment, the abrading particulate sensing means senses the relative presence of abrading particulate along a length of the detection zone. The system further includes a venturi orifice upstream from the abrading particulate sensing means through which supplied air and suspended abrading particulate is passable. The venturi orifice has a venturi diameter and the dispensing tip has a dispensing diameter; the venturi diameter being at least one-half as great as the dispensing diameter. In at least one embodiment, the dispensing diameter can measure between 0.007 and 0.026 inches. In a preferred embodiment, the dispensing diameter measures approximately 0.015 inches. Furthermore, the abrading particulate sensing means is an electronic sensor in one particular embodiment. Alternatively, the abrading particulate sensing means may be an ultrasonic turbidity meter. In still another embodiment, the ultrasonic turbidity meter and the ultrasonic agitator directed at the venturi cup share a common ultrasonic wave source.

In another embodiment, the dental air-abrasion system encompasses an automated controller for processing sensed abrading particulate information from the abrading particulate sensing means. The automated controller is capable of regulating fluid flow rates in the primary air passageway and the secondary air passageway for establishing a substantially uniform air suspended abrading particulate flow rate in the uniform particulate delivery passageway. A primary fluid flow regulator is included in the inlet conduit which is responsive to the automated controller and is used for restricting fluid flow through the primary air passageway. A secondary fluid flow regulator in the bypass conduit is similarly responsive to the automated controller and can restrict fluid flow through the secondary air passageway. The primary and secondary fluid flow regulators are each remotely actuatable valves responsive to commands issued from the automated controller.

DETAILED DESCRIPTION OF THE PREFERRED EMBODIMENTS

Figure 1:
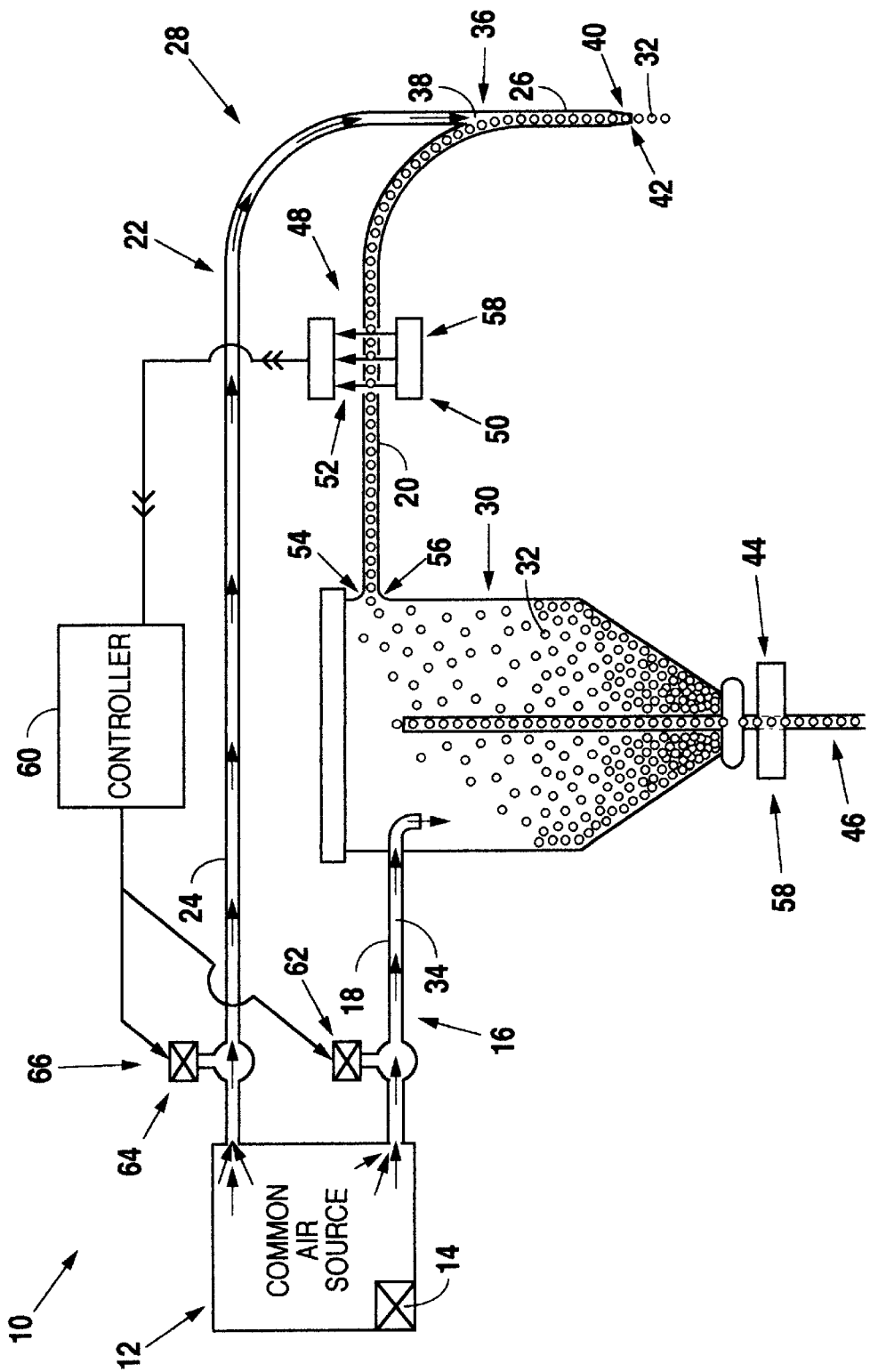
FIG. 1 is a schematic diagram of the cooperative components of the present invention arranged in a preferred embodiment as disclosed herein.

As required, detailed embodiments of the present invention are disclosed herein; however, it is to be understood that the disclosed embodiments are merely exemplary of the invention that may be embodied in various forms. The FIGURE(s) are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Certain terminology will be used in the following description and claims to relate relative orientations. Examples of such terminology include "upwardly", "downwardly", "rightwardly" and "leftwardly". The words "inwardly" and "outwardly" will refer to directions toward and away from, respectively, the geometric center of the structure being referred to. This terminology will include these words, specifically mentioned derivatives thereof, and words of similar import.

In the claims, components of the invention may be recited as being "coupled"; use of this terminology indicates that it is anticipated that elements of the invention may be connected together in such a way that there are other components interstitially located between the connected elements or that the elements may be connected in fixed or movable relation one to the other.

Referring to FIG. 1, one embodiment of the present invention is illustrated. A dental air-abrasion system 10 is shown having at least one air source 12. In the preferred embodiment, there is a single common air source 12, however, it is contemplated that a plurality of sources 12 may be utilized. The air source 12 supplies air to at least two passageways: a primary air passageway 16 and a secondary 22 air passageway. Air passing through the primary air passageway establishes a primary air flow 34 and the air passing through the secondary air passageway 22 establishes a secondary air flow. The supplied air is mixed with abrading particulate 32 in a venturi cup 30. Because the particulate 32 is very fine, having sizes in the 25 to 50 micron range, the air with which it is mixed must be very pure. Therefore, a purifier 14 is optionally incorporated into the air source 12 or is associated therewith to assure that all potentially fouling matter is removed from the air before being supplied to the system 10.

Pressured air is directed from the source 12 to an inlet conduit 18 of the primary air passageway 16 and into the venturi cup 30. The exit port for the air into the cup 30 is directed downward into the particulate 32 so the a "stirring" of the particulate 32 is affected by the entering air stream. To assist this stirring action, an ultrasonic agitator 44 may be optionally added to the venturi cup 30 that aids in the suspension of the particulate 32 and assures that compaction of the particulate 32 is prevented within the retaining cup 30. The ultrasonic agitator may be replaced by a mechanical reed valve agitator, electronic vibrator or other agitator means. That same air exits the venturi cup 30 into an exit conduit 20, passing through a venturi orifice 54. The cup 30 also includes a particulate inlet 46 port and structure through which particulate 32 may be added during the system's 10 operation.

During operation of the system 10, there is no assured uniformity with which the particulate 32 will exit the venturi cup 30 and enter the venturi orifice 54. As a result, previously known venturi cups have been susceptible to clogging because of the relatively small size of the venturi orifices 54; typically on the order of 0.007 inches in diameter 56. The present invention makes it possible for the dental air-abrasion system 10 to operate so that less air must actually pass through the venturi cup 30 and therefore the diameter 56 of the venturi orifice 54 may be enlarged.

From the venturi orifice 54, the primary air stream passes through the exit conduit 20. It is desired to know the flow rate or density of the particulate 32 passing through the exit conduit 20. Therefore an abrading particulate sensing means 48 is installed adjacent to, and across the exit conduit 20. The sensor 48 detects the amount of particulate 32 present in a detection zone 52. By taking sequential readings, particulate 32 flow rates may be established with respect to time. In at least one embodiment, the sensing means 48 takes the form of an ultrasonic turbidity meter 50. In another embodiment, an electronic sensor may read the air stream. The turbidity meter 50 operates by emitting a known strength ultrasonic wave from an ultrasonic wave source 58 that is detected after passing across the zone 52 of interest. By sensing how much of the ultrasonic wave was blocked by the presence of particulate 32, the amount of the particulate 32 present in the zone 52 may be determined. If these readings are taken sequentially and quickly at regular or known time intervals, a flow rate may be determined. This detected information may be transmitted to an automated controller 60 that in a preferred embodiment is a computerized controller 60 where the collected information is processed and analyzed and used as "driving" information for other functions of the system 10 that have been and will be discussed in greater detail herein.

A bypass conduit 24 of the secondary air passageway 22 is connected in parallel with the primary air passageway 16 between the air source 12 and a manifold 36 at which the two passageways 16,22 are joined into one single uniform particulate delivery passageway 26 at a fluid juncture 38. In the dental air abrasion system 10, the fluid juncture 38 is an air stream juncture. In this manner, a parallel air flow path 28 is established in the dental air-abrasion system 10.

The particulate 32 density information obtained from the sensing means 48 is used to control two remotely actuatable valves 66; a primary fluid flow regulator 62 positioned across the primary air passageway 16 and a secondary fluid flow regulator 64 positioned across the secondary air passageway 16. By appropriately controlling each of the air flow rates by independently opening and/or closing the valves 66, variations in particulate 32 load may be smoothed by adjusting the mix of pure air added downstream from the sensor 48 at the fluid juncture 38 between the primary 34 and secondary air flows.

The combined air flows pass from the juncture 38 through the delivery passageway 26 to a dispensing tip 40 located at a distal end thereof. The dispensing tip 40 is sized to assure that the particulate 32 being dispensed approaches supersonic characteristics upon exit. This is accomplished primarily from specifically sizing the diameter 42 of the tip 40. It is common for the diameter 42 of the dispensing tip 40 to be between 0.007 inches and 0.026 inches across. In those previously known devices, it was necessary to restrict the diameter 56 of the venturi orifice 54 to approximately one-half that of the dispensing tip 40. This constraint has been relieved by the parallel air flow paths and therefore it is possible in the present invention for the diameter of the venturi orifice 54 to be less than one-half that of the dispensing tip 40.

What is claimed is:

1. A dental air-abrasion system, said air-abrasion system comprising:

at least one air source for supplying pressured air to at least a primary air passageway and a secondary air passageway;

said primary air passageway comprising an inlet conduit establishing fluid communication between said air source and a venturi cup, said venturi cup for containing abrading particulate to be suspended in a primary air flow passing within said primary air passageway;

said primary air passageway comprising an exit conduit establishing fluid communication between said venturi cup and a manifold;

said secondary air passageway comprising a bypass conduit establishing fluid communication between said air source and said manifold;

said manifold providing a fluid juncture for joining said primary air passageway with said secondary air passageway into a single uniform particulate delivery passageway, said uniform particulate delivery passageway terminating in a dispensing tip; and an agitator coupled to said venturi cup for preventing compaction of abrading particulate in said venturi cup and for facilitating suspension of the abrading particulate in an air flow passing out of said venturi cup into said exit conduit.

2. The dental air-abrasion system as recited in claim 1, wherein said primary and said secondary air passageways together form a parallel air flow path between said air source and said manifold.

3. The dental air-abrasion system as recited in claim 1, wherein said at least one air source is a single common air source in simultaneous fluid communication with both of said primary and secondary air passageways.

4. The dental air-abrasion system as recited in claim 1, wherein said at least one air source further comprises a purifier for cleansing supplied air before introduction of the air into said primary and secondary air passageways.

5. The dental air-abrasion system as recited in claim 1 wherein said agitator is an ultrasonic agitator.

6. The dental air-abrasion system as recited in claim 1, wherein said venturi cup further comprises a particulate inlet through which additional abrading particulate is addable to said venturi cup during operation of said dental air-abrasion system.

7. A dental air-abrasion system, said air-abrasion system comprising:

at least one air source for supplying pressured air to at least a primary air passageway and a secondary air passageway;

said primary air passageway comprising an inlet conduit establishing fluid communication between said air source and a venturi cup, said venturi cup for containing abrading particulate to be suspended in a primary air flow passing within said primary air passageway;

said primary air passageway comprising an exit conduit establishing fluid communication between said venturi cup and a manifold;

said secondary air passageway comprising a bypass conduit establishing fluid communication between said air source and said manifold;

said manifold providing a fluid juncture for joining said primary air passageway with said secondary air passageway into a single uniform particulate delivery passageway, said uniform particulate delivery passageway terminating in a dispensing tip; and an abrading particulate sensing means directed across said exit conduit for sensing an amount of abrading particulate present in a detection zone within said exit conduit.

8. The dental air-abrasion system as recited in claim 7, said system further comprising:

a venturi orifice upstream from said abrading particulate sensing means through which supplied air and suspended abrading particulate is passable.

9. The dental air-abrasion system as recited in claim 8, wherein said venturi orifice has a venturi diameter and said dispensing tip has a dispensing diameter, said venturi diameter being at least one-half as great as said dispensing diameter.

10. The dental air-abrasion system as recited in claim 9, wherein said dispensing diameter is at least 0.007 inches across.

11. The dental air-abrasion system as recited in claim 10, wherein said dispensing diameter is less than 0.026 inches across.

12. The dental air-abrasion system as recited in claim 7, wherein said abrading particulate sensing means directed across said exit conduit for sensing an amount of abrading particulate present in a detection zone within said exit conduit measures relative presence of abrading particulate along a length of said detection zone.

13. The dental air-abrasion system as recited in claim 7, wherein said abrading particulate sensing means is an ultrasonic turbidity meter.

14. The dental air-abrasion system as recited in claim 13, said system further comprising:

an agitator coupled to said venturi cup for preventing compaction of abrading particulate in said venturi cup and for facilitating suspension of the abrading particulate in an air flow passing out of said venturi cup into said exit conduit.

15. The dental air-abrasion system as recited in claim 14, wherein said ultrasonic turbidity meter and said ultrasonic agitator directed at said venturi cup share a common ultrasonic wave source.

16. The dental air-abrasion system as recited in claim 7, wherein said abrading particulate sensing means is an electronic sensor.

17. The dental air-abrasion system as recited in claim 7, said system further comprising:

an automated controller for processing sensed abrading particulate information from said abrading particulate sensing means, said automated controller capable of regulating fluid flow rates in said primary air passageway and said secondary air passageway for establishing a substantially uniform air suspended abrading particulate flow rate in said uniform particulate delivery passageway.

18. The dental air-abrasion system as recited in claim 17, said system further comprising:

a primary fluid flow regulator in said inlet conduit responsive to said automated controller for restricting fluid flow through said primary air passageway.

19. The dental air-abrasion system as recited in claim 18, said system further comprising:

a secondary fluid flow regulator in said bypass conduit responsive to said automated controller for restricting fluid flow through said secondary air passageway.

20. The dental air-abrasion system as recited in claim 19, said system further comprising:

said primary and said secondary fluid flow regulators each being remotely actuatable valves responsive to commands issued from said automated controller.

21. A dental air-abrasion system, said air-abrasion system comprising:

an air source for supplying pressured air to a primary air passageway and a secondary air passageway;

said primary air passageway comprising an inlet conduit establishing fluid communication between said air source and a venturi cup, said venturi cup adapted for containing abrading particulate to be suspended in a primary air flow passing within said primary air passageway;

said primary air passageway comprising an exit conduit establishing fluid communication between said venturi cup and a manifold and said secondary air passageway comprising a bypass conduit establishing fluid communication between said air source and said manifold;

an abrading particulate sensor directed across said exit conduit for sensing an amount of abrading particulate present in a detection zone within said exit conduit; and a fluid flow regulator adapted to be operatively controlled based on information sensed by said abrading particulate sensor.

22. The dental air-abrasion system as recited in claim 21, wherein said fluid flow regulator is positioned in said bypass conduit for regulating fluid flow in said bypass conduit.

* * * * *